United States Patent [19]

Waxman

[11] 4,058,001
[45] Nov. 15, 1977

[54] ULTRASOUND IMAGING SYSTEM WITH IMPROVED SCAN CONVERSION

[75] Inventor: Albert S. Waxman, Santa Clara, Calif.

[73] Assignee: G. D. Searle & Co., Skokie, Ill.

[21] Appl. No.: 710,942

[22] Filed: Aug. 2, 1976

[51] Int. Cl.² .................. G01N 29/00; A61B 10/00
[52] U.S. Cl. .............................. 73/620; 128/2 V; 358/112; 73/629
[58] Field of Search .............. 73/67.8 S, 67.8 R, 67.7, 73/67.5 R, 71.5 US; 128/2 V, 2.05 Z; 358/112

[56] References Cited

U.S. PATENT DOCUMENTS

| | | | |
|---|---|---|---|
| 3,856,985 | 12/1974 | Yokoi et al. | 128/2 V |
| 3,857,052 | 12/1974 | Beller | 73/67.8 S |
| 3,954,098 | 5/1976 | Dick et al. | 128/2 V |

Primary Examiner—Richard C. Queisser
Assistant Examiner—Stephen A. Kreitman
Attorney, Agent, or Firm—Walter C. Ramm; Albert Tockman; Dennis O. Kraft

[57] ABSTRACT

In an improved system for medical imaging employing a transducer for transmitting and detecting ultrasonic vibrations, a digital scan converter accepts echo signals detected by the transducer and transducer position signals identifying the point of origin of the signals in a scanning plane transversely oriented relative to the body of the patient under study. The amplitudes of the echoes detected are stored at memory locations associated with the points of origin of the echoes. Peak detection analysis is performed on large echoes emanating from higher impedance tissue interfaces within the scanning plane, while cumulation and normalization analysis is performed on small echoes emanating from low impedance tissue interfaces within the scanning plane. Sensitivity to otherwise unobtainable image details, signal to noise ratio, and freedom from distortions is maximized, yet the improved system may be used 12 Claims, 3 Drawing Figures

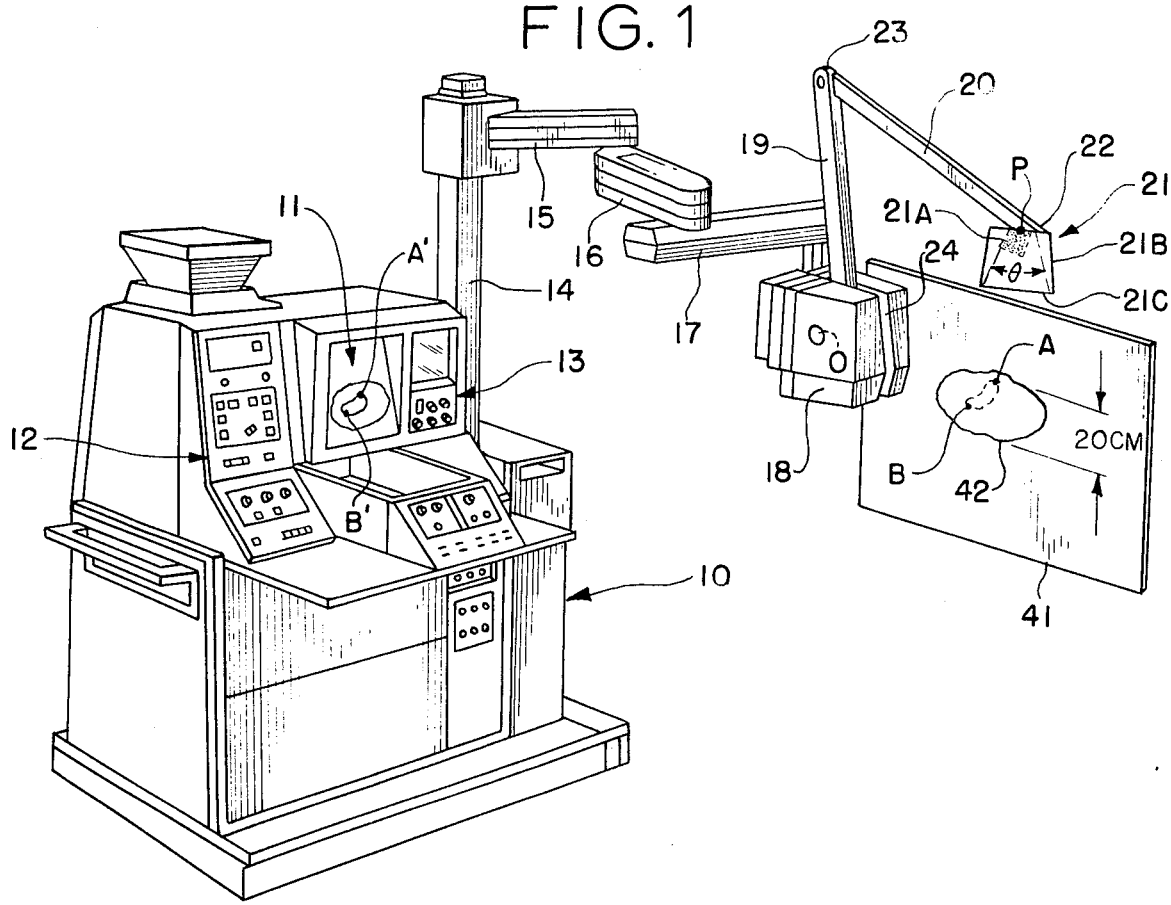

FIG. 1

PREREQUISITE AMPLITUDE AT .4Db

| LOCATION | New Echo Amplitude From Location | Prior Contents of Memory Storage 27 at Location Address | Processing | Final Contents of Memory Storage 27 at Location Address |
|---|---|---|---|---|
| A | .100 Db | 0 | INTEGRATE AT 37 | .100 |
| A | .200 | .100 | INTEGRATE-NORMALIZE AT 37 | .150 |
| A | .500 | .150 | PEAK ANALYSIS AT 35 | .500 |
| A | .200 | .500 | COMPARE AT 39 | .500 |
| A | .550 | .500 | PEAK ANALYSIS AT 35 | .550 |
| B | .02 | 0 | INTEGRATE-NORMALIZE AT 37 | .02 |
| B | .05 | .02 | INTEGRATE-NORMALIZE AT 37 | .035 |
| B | .10 | .035 | INTEGRATE-NORMALIZE AT 37 | .057 |
| B | .06 | .057 | INTEGRATE-NORMALIZE AT 37 | .058 |
| B | .04 | .058 | INTEGRATE-NORMALIZE AT 37 | .054 |

FIG. 3

ULTRASOUND IMAGING SYSTEM WITH IMPROVED SCAN CONVERSION

BACKGROUND OF THE INVENTION

This invention is directed toward an improved form of an ultrasonic imaging system for use in medical diagnosis.

Ultrasonic detectors have gained increased usage in the medical community for providing visual representations of detected tissue interfaces in a plane which transversely intersects the body of a living subject. Ultrasonic imaging is advantageous in that it provides a rapid and painless means of searching for abnormalities in the location or structure of tissue interfaces. Because of the high speed of ultrasonic analysis, ultrasonic studies are of particular value in imaging organs which tend to shift or move. Ultrasonic studies of cardiac conditions and stomach, liver and kidney ailments, have provided a means of obtaining reliable information which has heretofore been unattainable.

Many commercial ultrasonic imaging units employ some form of analog scan converter. One such scan converter is depicted in U.S. Pat. No. 3,864,661. Such scan converters typically use a storage tube which employs a cathode to generate a beam of electrons focused on an anode to produce a distribution of electrostatic charge thereon in a pattern representative of the tissue interfaces detected within the body of the patient. The pattern of charges is "read" from the cathode of the storage tube and concurrently displayed in the form of an image on a conventional television receiver.

The video images displayed on the television receiver may be in the form commonly referred to as a "B" scan. B scans depict cross-sectional areas of the patients under study in the plane of the ultrasound probe (typically a vertical plane). Echoes received from particular coordinate locations in this plane are depicted as spots of light on the television receiver. Coordinate locations from which no echoes are received, result in an absence of illumination on the display unit. Because of background noise, an amplitude demarcation is necessary to determine which signals are to be selected for display as echoes, and which signals are background and should be suppressed.

B scan displays may be derived from one or two different forms of pulse processing techniques in conventional ultrasonic imaging systems. The echo pulses attributed to any particular coordinate location within the body of the patient may be integrated, so that the display at the corresponding point on the display unit represents the amplitude sum of all of the pulses deem to have originated from that point. The information obtained from this form of display, however, is subject to a high degree of variation from operator techniques in moving the ultrasonic probe across the body of the patient. If the probe dwells too long in a single position, the echoes detected from the locations scanned at that probe position will be weighted out of proportion to echoes from points which are scanned more rapidly. By the same token, if particular locations are not scanned at all or scanned for a shorter period of time, the detected echoes will reflect an inadequate sampling from that position.

To obviate this problem, a different technique was developed. This technique is known as pulse amplitude peak detection and is characterized in that only the largest echo signal is registered from each coordinate location. In this way, the ultrasound diagnostic unit becomes more nearly operator-independent. Excessive sampling of some locations and inadequate sampling of other locations does not result in distortions, since only the largest echo amplitude peak from each coordinate location will be ultimately registered on the display unit. The echo amplitude peak detection technique has been used to wide advantage in ultrasound medical imaging.

It has been found, however, that when ultrasound diagnostic units having conventional analog scan converters are adapted for echo amplitude peak detection, the full advantages which might be expected from the peak detection technique are not realized. Generally reduced resolution is found in peak, detection mode, especially when an image portion is over-scanned, and because edge resolution is less than center resolution. The image will tend to be less clear toward the edges due to the growth of spot size in the storage tube, and the tubes inherently exhibit non-uniformities of 10% typically. Image alignment is difficult due to poor gray scale matching and geometry distortions.

The write speed of ultrasonic units equipped with analog scan converters is limited, so that in order to avoid loss of echo information due to this lack of speed, larger fields of view than optimum for particular applications must be used. Even so, all of the available echo information may not be registered on the storage tube, and in any event resolution is degraded. Further, writing speed limitations, along with the characteristic long erase time of the analog converter, are significant enough to prevent practical real time imaging.

Another facet of the foregoing problem is the distinct time interval between read and write, which functions cannot be done simultaneously with the foregoing systems. This need to multiplex the read and write functions result in image artifacts, particularly a "venetian blind" effect, on the CRT monitor. That is, the monitor goes blank and blinks during the erase interval just prior to a new information recording operation. This effect is, of course, distracting to those viewing the monitor. Finally, post-image processing and analysis is difficult, since the entire system and associated circuitry is in analog form.

Moreover, this improvement which is possible with peak detection, while significant, does not by any means exhaust the possibilities of improving image quality. The tissue sought to be studied may include both strong, specular scatterers of ultrasonic energy, and diffuse spherical scatterers; on the macroscopic level, the former may be thought of as a high acoustic impedance interface, and the latter as a low acoustic impedance interface. Peak detection helps mostly with the former, by discriminating in favor of the strongest echo, that normal to the addressing acoustic pulse.

In the case of the diffuse scatterers, (or low impedance interfaces), however, good image information may continue to be lost, since a location associated with such a scatterer or interface does not provide an echo which is significantly larger or more representative than the others from such location. Such diffuse scatterers or low impedance interfaces are precisely those which characterize those tissue formations which are the most difficult to analyze, such as the internal portions of organs having fairly similar or uniform structures, or tumors which are similar to surrounding healthy tissues. Accordingly, any lacks in this regard can have serious diagnostic consequences.

SUMMARY OF THE INVENTION

It is an object of the present invention to provide ultrasound imaging system which exhibits improved sensitivity to interfaces between similar tissues in the body of the patient under study, as well as concurrently exhibiting improved sensitivity to interfaces of dissimilar tissues.

It is also an object of the invention to provide an ultrasound imaging system which achieves the foregoing improved sensitivity while providing both a real time display capability and a static display capability.

It is a related object of the invention to provide, in an ultrasound imaging system, an improved echo amplitude peak detection capability.

It is another related object of the invention to provide an cumulation and normalization analysis capability to enable the use of relatively small echo amplitudes in improving image resolution.

A further object of the invention is to improve the speed with which data may be written into or erased from the system.

Another object of the invention is to provide a scan converter with improved resolution, uniformity and multiple image storage capability.

A still further object of the invention is the provision in an ultrasound imaging system of a digital scan converter having improved sensitivity and resolution.

BRIEF DESCRIPTION OF THE INVENTION

In one broad aspect this invention is, in an instrument for use in medical diagnosis having a transducer for transmitting vibrations at ultrasonic frequencies into the body of the patient and for detecting echoes produced at tissue interfaces within a patient by said vibrations and for generating responsive electrical signals, and a display unit for producing a two-dimensional visual representation of the tissue interfaces in a scanning plane, the improvement comprising a digital scan converter for receiving inputs from the transducer and having location determination means for assigning two-dimensional coordinates in the scanning plane and having addressable memory storage locations in communication with the transducer for storing representations of the amplitudes of the echo signals at corresponding memory storage locations having the addresses of the aforesaid two-dimensional coordinates, and circuit means for communicating the stored representations to the display unit.

With the digital scan converter associated in the foregoing manner with the system, a greatly improved degree of sensitivity and resolution is attained, the non-uniformities and distortions, both of linearity and of gray scale, found in the analog converter are avoided, multiple image storage capability is improved, and write and erase speed are improved to permit real time imaging.

In another aspect this invention may be considered to be an apparatus or method of detecting a location of tissue interfaces in the body of a living subject using a ultrasonic imaging system employing a proble, probe position sensing means, and a display unit wherein image signals are registered at a multiplicity of spaced locations comprising: directing vibrations at ultrasonic frequencies from the probe into the body of the subject, detecting the occurrence and timing of the resulting echoes, associating specific two-dimensional coordinate positions in a plane transverse to the body of the subject with specific ones of the spaced locations in the display unit as determined by the positions of the probe ascertained from the probe position sensing means and as determined by the distances of the origin of the echoes from the probe as ascertained from the echo timing, registering as echo signal at each of the associated spaced locations on said display unit only the largest single echo at each one of the aforesaid multiplicity of spaced locations associated with a specific two-dimensional coordinate position at which any echo achieving a pre-selected prerequisite amplitude is detected, and registering the normalized value of the amplitudes of echoes emanating from each two-dimensional coordinate position at which no echo achieves the prerequisite amplitude.

The digital scan converter improvement permits and facilitates the incorporation of this improvement of peak detection operation for larger pulse echo amplitudes, and the integration-normalization analysis for smaller amplitudes. These techniques provide great improvement in the quality of the ultimate diagnostic image produced. Small echo amplitudes emanating from interfaces between similar tissues bearing useful image information would normally be lost in the peak detection mode. In this invention, however, they are saved, cumulated and normalized to obtain values for particular locations which significantly exceed background noise and thus become useful, particularly in visualizing slight discontinuities within the tissue of a patient which would otherwise be obscured. Gray scale possibilities and resolution, especially for those details which are most difficult to detect, are greatly improved. At the same time, inaccuracies in the contribution of large pulses are effectively controlled by the peak detection technique. The inherent speed of the digital scan converter allows echo information processing in either static mode or real time, along with all of the advantages set forth above.

DESCRIPTION OF THE DRAWINGS

The mode of operation of the invention and the nature thereof may be more specifically ascertained by reference to the accompanying drawings in which:

FIG. 1 is a perspective view of an ultrasonic imaging system according to this invention, including a typical imaging plane and cross-section of a patient sought to be examined;

FIG. 3 is a tabulation of values pertaining to location A and B in the patient cross-section of FIG. 1 showing the operation of the pulse processing of the present invention.

DETAILED DESCRIPTION OF THE DRAWINGS

Figure 2:
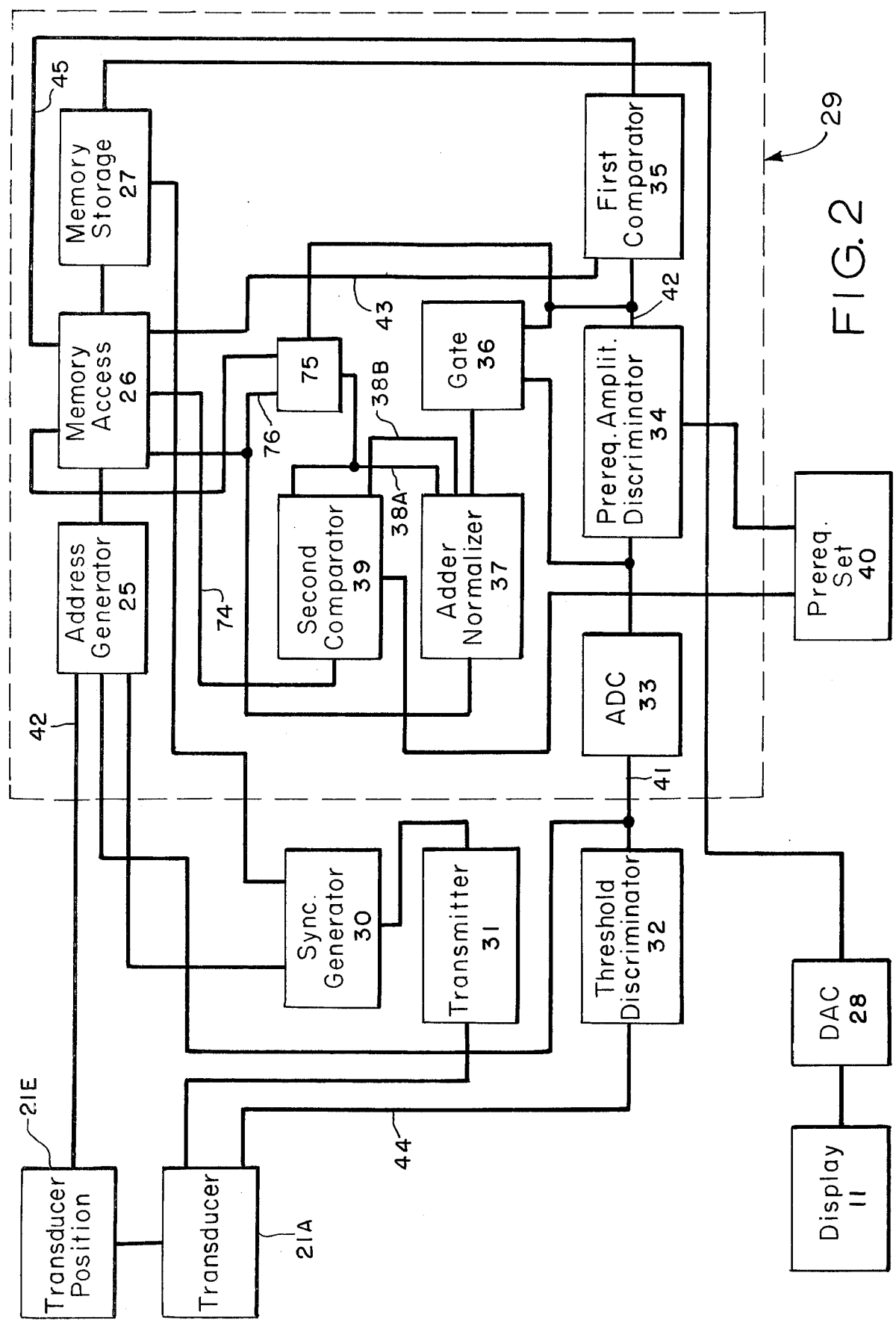
FIG. 2 is a block diagram of the electrical elements of the system of FIG. 1 including a digital scan converter.

Referring more particularly to FIG. 1, there is illustrated an instrument for medical diagnosis using ultrasound and having a console 10 housing the major electrical components thereof. A control panel 12 is provided for entering patient identification, a prerequisite amplitude useful in alternative forms of pulse processing, and other operator controls. A second control panel 13 is provided from which adjustments, calibrations and other equipment functions may be performed with respect to the control of the image produced on the display unit 11, the visible portion of which is a conventional television receiver. From an upright standard 14 a series of arms, 15, 16 and 17 are provided which terminate in a probe control unit 18. A probe positioning arm 19 extends from probe control unit 18 and is joined to a second probe positioning arm 20, from the extremity of which the probe assembly 21 extends. Within the probe control unit 18 there is located a first probe position sensor unit 24 connected to the arm 19. Between the arms 19 and 20 there is located a second probe position sensor 23, and between the arm 20 and probe assembly 21 there is located a third probe position sensor 22. Collectively, the position sensors 22, 23 and 24 provide information to the ultrasonic imaging system which locates the exact position and orientation of probe assembly 21. This is achieved since each of the position sensors 22, 23 and 24 define the exact angular orientation of the members to which they are connected and since the lengths of the arms 19 and 20 are known precisely. The rotational axis of the arm 19 within the control unit 18 may be considered to be the point of origin labelled 0 in FIG. 1.

Probe assembly 21 may comprise a simple transducer assembly for beaming ultrasound addressing pulses into a patient, and for receiving the returning echo pulses returning from tissue interfaces within the patient along the path of the original addressing pulse. Such a transducer is entirely satisfactory for static imaging, in which the probe is manually scanned over the skin of a patient. In such a scan, the plane of movement of the arms 19 and 20, and the probe assembly 21, defines a scanning plane 41 within which the probe moves, and from within which echoes are detected in response to the addressing ultrasound pulses. The plane 41 is transversed to the body of the patient, and the outline of the patient is depicted as a closed curve 42 representing the interface of the skin of the patient with his external environment. The thickness of the patient's torso is approximately 20 centimeters as indicated in FIG. 1. The intersection of scanning plane 41 with the patient also, of course, defines the cross-section of the patient of which at least a portion is ultimately imaged on the TV monitor.

If real-time imaging is to be performed, the probe assembly 21 is somewhat more complex then indicated above. In both modes, the assembly can comprise a transducer 21A which interfaces with a fluid in container 21B, with the fluid being acousticly coupled to the patient by membrane 21C. But in the real-time mode, the transducer 21A is driven by reciprocation means to oscillate back-and-forth about pivot point P through an angle $\theta$. In this mode, it is the angle $\theta$ which defines scanning plane 41, and the probe assembly 21 is normally positioned and maintained at a stationary position on the patient's body adjacent an organ to be imaged during a dynamic study thereof. Other means also may be used to provide real time echo information to the system besides the above mechanically swept arrangement; for example, a phased array of transducers, which may be electronically swept to interrogate a sector of scanning plane 41, also may be used.

In the case of the static mode, the transducer collects and transmit echo signals whose amplitudes vary with time; these signals are correlated to locations determined from the angular orientation of arms 19 and 20 (detected by sensors 22, 23 and 24) and internal timing circuity which, given the speed of sound in the body, calculates the distance between the transducer and the tissue interface within scanning plane 41. The foregoing probe position sensors, together with the timing circuitry, comprises an echo signal location determining means which effectively assigns two-dimensional coordinates to the points in the scanning plane 41 from which echoes emanate in response to the transmitted pulses. Thus, echoes emanating from points A and B respectively in scanning plane 41 are represented as points A' and B' on the display unit 11.

In the real-time imaging mode, sensors 22, 23 and 24 continue to be useful in providing probe assembly position information, but the location of the echo signal is determined by relating the angular orientation of the probe to the time-varying amplitude information being delivered by the transducer in response to returning echo information. From such angular information, the internal timing circuitry, given the speed of sound in the body, determines the coordinates of the points in the scanning plane 41 from which the returning echo information emanated.

Referring now to FIG. 2, a block representation of the ultrasonic imaging system of FIG. 1 is illustrated. Transmitter 31 is connected to the transducer 21A for driving it to address penetrating ultrasonic vibrations into the patient's body. Transmitter 31 is controlled by a sync generator 30 which operates the transmitter 31 in synchronization with an address generator 25. The transducer 21A detects the resultant echoes indicative of the location and nature of tissue interfaces in the imaging plane 41 (FIG. 1). Upon receiving responsive echoes indicative of tissue interfaces, transducer 21A produces representative echo signals which are conducted by way of line 44 to a threshold discriminator circuit 32. Signals which are not of the threshold magnitude, established at a level which is considered to be background noise, are blocked from further processing. Signals which equal or exceed the threshhold level are passed to the digital scan converter 29.

The digital scan converter includes a multiplicity of addressible memory storage locations in the memory storage 27, as well as an address generator 25. Address generator 25 receives the echo signals from threshhold discriminator 32, as well as the input of transducer positioning means 21E, which includes the transducer reciprocating means (in the real time mode), and other positional inputs, including signals from the probe position sensors 22, 23 and 24. Address generator 25 digitizes the signals to generate a digital location address as defined by the position and orientation of the transducer, and by the interval of return of the echo signal after transmission of the ultrasonic vibration which causes it. The address produced is correlated through memory access 26 to an address in the memory storage unit 27. Also included as a part of digital scan converter 29 is an analog-to-digital converter 33 for producing digital representations of the amplitudes of echo signals received from transducer 21A through threshhold discriminator 32.

Much of the remainder of the scan converter to be described involves an improved combination of echo signal peak detection means along with a cooperating pulse accumulating and normalization means. The peak detection portion comprises an amplitude discriminator 34, and a first comparator circuit 35, working in cooperation with the above-mentioned memory and address components. In the operation of the peak detection, the digital representations of echo signals produced by converter 33 are passed to amplitude discriminator 34. Discriminator 34 is connected to a prerequisite amplitude control 40, upon which a desired discrimination or prerequisite amplitude is selected. The amplitude level thus selected is used by discriminator 34 as a criteria for separating incoming echo pulses. Thus, those echo pulses received by discriminator 34 which achieve the prerequisite amplitude are passed on to first comparator 35, whereas those echo signals which do not achieve that prerequisite amplitude are blocked by discriminator 34 from passing into comparator 35.

The signals above the prerequisite are directed into the peak analysis circuitry, and those which do not are considered as relatively small signals which are separated therefrom and processed by the accumulation and normalization circuitry, as will later be explained. At this point, it is sufficient to note that incoming signals to discriminator 34 are also simultaneously passed through gate 36. Gate 36 includes an inhibit input, which is connected to the output of discriminator 34. The output of gate 36 feeds the input of the pulse accumulating and normalizing circuitry to be explained. In this manner, gate 36 functions to close off the input to the pulse accumulating circuitry whenever discriminator 34 determines that the incoming echo signal is large enough to pass through the discriminator and be processed by the peak detection circuitry.

Meanwhile, memory access circuit 26 receives the address generated by address generator 25 in response to an incoming echo signal, interrogates memory storage 27, and registers from the memory storage any values contained therein which may have been previously stored at that address location in the memory storage. The memory access unit 26 then transfers both the address and the registered memory contents at that address location to first comparator 35 via connector 43, (as well as to a second comparator 39 via connector 74 associated with the accumulation-normalization circuitry; see below).

The larger signals which have achieved the prerequisite amplitude and thus pass through discriminator 34 are then compared by first comparator 35 with the previously stored contents of the memory storage for the address location associated with the new echo signal. First comparator 35 thereupon transmits to memory storage unit 27 by way of line 45 and memory access 26 either (1) the newly arrived echo signal received from discriminator 34, or (2) the previously stored contents of the memory storage at the same address location associated with the new echo signal, whichever is greater. Of course, it may be that the incoming echo signal is below the prerequisite amplitude set by control 40, and thus no signal is passed by discriminator 34. In that event, the previously stored contents of the memory at the address location of the incoming echo signal remain the same, except for a possible change due to the action of the accumulation-normalization circuitry. In this manner, for those echo signal locations for which the peak detection circuitry receives new echo pulses greater than the selected prerequisite amplitude, the memory storage retains only the largest signal, the lesser being discarded. The system thus is greatly improved in recording and displaying those peak values most accurately characterizing the tissue being examined, as well as improving independence from scanning and sampling variations introduced because of differences in operator techniques.

The improved digital converter of the invention at the same time as it performs the above peak analysis on large echo signals also extracts further useful image information by utilizing echo signals which are below the prerequisite amplitude and which would otherwise be discarded. The cumulating and normalizing circuitry which will now be described utilizes these signals to effectively increase the image content for such locations relative to noise and background at that location, thus producing a vastly improved image. This is particularly so where large amplitude echo signals are simply not produced because of the nature of the organ being visualized, which may for example, comprise diffuse scatterers of acoustic energy, or (on a macroscopic level) tissue interfaces of low impedance. Thus, when the amplitude of the echo signals received by discriminator 34 does not achieve the prerequisite amplitude, discriminator 34 produces no inhibiting output to gate 36. The echo signal, which is present at gate 36 because of the connection between gate 36 and converter 33, then passes through gate 36 to the adder-normalizer circuit 37.

Meanwhile, as has been described as above, upon receipt of an address from address generator 25, the memory access circuit draws from memory storage circuit 27 the contents of memory storage at that address location, and transfers these contents to second comparator circuit 39 by way of line 74. These memory contents are passed by comparator 39 to one input of gate 75 and also to an input of adder-normalizer 37 via line 38A. However, adder-normalizer 37 does not utlize this input unless enabled via line 38B by means of an appropriate actuating or enabling signal from the output of comparator 39.

If the stored contents of the memory at the address designated fails to exceed the prerequisite amplitude set upon control 40, second comparator 39 transmits an actuating signal to the adder 37. This output to adder-normalizer 37 is an integration signal, which actuates the adder-normalizer to recognize the new echo signal and add it to the previously stored contents of the memory (received by adder-normalizer 37 via line 38A) for that location. The sum of the new echo signal and the previous contents for that location is then arranged by the number of occurrences of such echo signals from that location, to achieve a normalized value for that location. An output indicative of this normalized value is then directed by the enabled adder-normalizer 37 to memory access 26 (and hence storage 27) via line 76, while the same output is also directed via line 76 to gate 75 as an inhibiting signal.

Inhibiting the gate 75 in this manner prevents restorage of the previously stored contents registered upon second comparator 39, to which gate 75 is also connected. Instead, memory access 26 directs the new normalized value for the location in question to the storage. This new normalized value then becomes the value for the particular location against which subsequent echo signals for that location will be compared by both the peak detection and the accumulation-normalization circuitry. As long as incoming new echo signals for a given location are below the prerequisite amplitude, and the value of the storage signal for that location has not yet exceeded the prerequisite amplitude, the foregoing summation-normalization circuitry functions to build up the imaging value of the stored content for such locations out of newly arriving echo signals which would otherwise individually be too weak to contribute to the resultant image. It will be appreciated that this process very much aids in de-emphasizing the noise content at the locations where the signals are thus summed and normalized. Noise tends to be random, or non-recurring, and if subsequently occurring at the location, it may be oppositely going as compared to an earlier occurrence. A true information-bearing signal, on the other hand, will tend to be repetitive and coherent. These characteristics are exploited by the summing and averaging both to average out noise with its incoherent tendencies, while reinforcing true information signals, and thus the signal to noise ratio.

Of course, in many instances the incoming echo signal for a particular location will be below the prerequisite amplitude. Thus while such a signal will appear at adder-normalizer 36, the contents of the memory storage at that location will already be greater than the prerequisite amplitude. In this event such an incoming signal is ignored, and the previous contents of the memory for that location persist. With reference to the FIG. 2 circuitry, second comparator 39, which of course receives the stored contents of the location in question, compares this input to the prerequisite amplitude value (from control 40). Since the storage signal is greater than the prerequisite amplitude, comparator 39 produces no actuating or enabling signal on line 38B to adder 37. Accordingly, adder-normalizer 37 does not recognize the new echo signal, and produces no output on line 76 into memory access 26, nor as an inhibit signal to gate 75. Thus gate 75 remains open, and through it the stored contents at that location, after a predetermined delay, are retransferred back to memory access unit 26 and again stored in storage 27 at the location indicated by the corresponding address of the arriving signal as given by generator 25.

In the manner, the foregoing accumulation-normalization circuitry allows only those incoming echo signals which fail to achieve the prerequisite amplitude to be added and normalized to the existing stored contents of the memory at the address corresponding to the incoming echo signal location, and then only at those memory storage locations in which the previously stored contents fails to exceed the prerequisite amplitude. This process continues, and small echo signals for a given location continue to be added and normalized to the previously stored values, and the newly augmented values stored, with an improving signal to noise ratio, until either the prerequisite amplitude is attained, or a large echo signal exceeding both the prerequisite amplitude and the stored memory contents is detected at that location.

Of course, if any new echo signal for a given location is greater than the prerequisite amplitude, it will be processed by the peak analysis portion of the circuitry described above. As has been seen, such a large pulse exceeding the prerequisite amplitude will be compared by the peak analysis circuitry to the stored contents (which may have been derived either through earlier accumulation-normalization or earlier peak detection) at that location, and only the greater of the two will be stored. When the memory at any particular location contains such a large value exceeding the prerequisite amplitude, this value remains until superceded by still larger value, and smaller echo signals associated with that location are thereafter not registered.

By way of example, and with reference to FIG. 3 an analysis of echoes received from locations A and B in FIG. 1 is illustrative of the signal processing in the digital scanner 29. In actual practice, of course, the echoes from location A would not all be sequential, nor would the echoes from location B, but they have been tabulated in this manner to illustrate the basis upon which final data is stored in memory storage 27.

If the prerequisite amplitude selected by use of circuit 40 is 0.4 decibels and the ultrasound scan is initiated, the initial contents of memory storage 27 will be zero at all locations. Thus, then the first echo signal of 0.100 decibels is received from location A, there is no output from prerequisite amplitude discriminator 34, so that the echo signal is passed through gate 36 to the adder-normalizer circuit 37. At adder-normalizer circuit 37 the amplitude of the new echo is integrated with the previously stored contents at location A, which of course was zero. Thus, the amplitude of the new echo signal comprises the entire output of adder-normalizer 37 and so is stored at location A in memory storage 27. A second echo of 0.200 decibels which is received likewise does not achieve the prerequisite amplitude. Therefore it is integrated in circuit 37 with the previously stored contents of location A and normalized by the number of events of such signals. The resultant normalized amplitude value of 0.150 decibels is stored at location A in memory storage 27.

When a larger pulse of 0.500 decibels is received, this pulse passes the prerequisite amplitude discriminator 34 and so produces an output at circuit 42. The gate 36 is thereby closed and the previously stored contents of the location A are compared with the amplitude of the new pulse in comparator 35. The amplitude of the new pulse, 0.500 db., is greater than the previously stored contents of 0.150 db., so that the amplitude of the new pulse only is stored at location A.

When a smaller pulse say of 0.200 db. is thereafter received, it fails to pass discriminator 34 and so is gated to the adder-normalizer circuit 37. However, second comparator 39 fails to provide an output to act as an integration or enabling signal to the adder-normalizer circuit 37 since the previously stored contents are greater than the prerequisite amplitude. Thus, the previously stored contents are merely recycled through second comparator 39 back to memory storage.

When a larger pulse of 0.550 db. is received, however, the contents of memory storage at location A changes. This larger pulse passes the discriminator 34 and produces an output which disables both gates 36 and 75 so that the only return to memory storage will be through line 45. Since the amplitude of the new echo signal is greater than the peak of the previously stored pulse, peak analysis is performed at comparator 35 and the amplitude of the new signal is stored at address A in memory storage 27.

At location B, only smaller echo signals are received from probe assembly 21, the signals ranging from 0.002 db. to 0.010 db. Since at no time does any single one of the echo signals achieve the prerequisite amplitude, nor does the stored contents at location B ever achieve the prerequisite amplitude, all pulse processing proceeds as integration-normalization, with gate 36 open and adder-normalizer circuit 37 summing the new echo signal and the previously stored contents for location B, and averaging over the number of smaller echo signals received for location B.

As in other ultrasound diagnostic instruments, the contents of the scan converter is sampled in synchronization with the raster of the television receiver 11. The contents of the scan converter are converted from digital to analog signals by digital to analog converter 28 so that a conventional analog television receiver may be utilized as the display unit 11. Unlike conventional scan converters, however, the processing time of the digital scan converter 29 is not limited by the scanning time of the television raster. Rather, the raster draws upon the contents of a buffer in the form of a memory storage 27 so that data acquisition and storage can proceed separately. In this way, data acquisition of echo signals is always completed, and is not terminated prematurely in order to accommodate the raster speed of the television receiver. This feature, too, significantly improves the quality of the data received.

Of course, the digital scan converter, along with its associated peak detection and integration-normalization signal processing, is inherently fast due to its digital nature, thus facilitating the writing and erasing of information and obviating time lags for real time imaging capability. Marked improvement in image uniformity, image alignment and multiple image handling capability is also inherently provided. The associated improvements in signal processing providing further image improvements and flexibility to adapt to changing imaging conditions and tissue interface types are a great diagnostic advantage. The distribution of echo signals to be processed by peak detection as opposed to accumulation-normalization may be varied by changing the prerequisite amplitude to suit imaging conditions. The improvement provided by the accumulation-normalization means in sensitivity to obscure details along with gray scale possibilities is matched to the peak detection so that the image is greatly optimized in signal to noise ratio, sensitivity and resolution for all types of tissue interfaces.

The foregoing illustrative examples of the embodiment of the invention depicted are for purposes of illustration only, and no unnecessary limitations should be construed therefrom, as the scope of the invention is defined by the claims appended hereto.

I claim:

1. In an ultrasonic instrument for use in medical diagnosis having a transducer for transmitting vibrations at ultrasonic frequencies into the body of a patient and for detecting echoes produced at tissue interfaces within said patient by said vibrations and for generating responsive electrical echo signals, and a display unit for producing a two-dimensional visual representation of said tissue interfaces in a scanning plane, the improvement comprising a digital scan converter for receiving inputs from said transducer and having location determination means for assigning two-dimensional coordinates in said scanning plane, and having addressable memory storage locations in communication with said transducer for storing representations of the amplitudes of said echo signals at corresponding memory storage locations having the addresses of the aforesaid two-dimensional coordinates, circuit means for communicating said stored representations to said display unit, and echo signal accumulation and normalization means accepting incoming echo signals having an amplitude less than a prerequisite amplitude, for comparing to said prerequisite the previously stored contents of said memory storage locations at the address corresponding to each said incoming signal, and, if said stored contents is less than said prerequisite, accumulating said incoming signal with said contents, normalizing the value thereby obtained by the number of occurrences of said accumulation and transmitting to said storage locations in normalized value thereby obtained for registration at said corresponding address.

2. In a system for medical imaging employing a probe for transmitting ultrasonic vibrations to a patient and for receiving responsive echoes indicative of tissue interfaces and for producing corresponding representative echo signals, probe position sensing means and a display unit for producing two-dimensional visual representations of said tissue interfaces in an imaging plane, the improvement comprising a multiplicity of addressable electronic memory storage locations in communication with said display unit, an address generator for receiving inputs from said probe position sensing means and for generating a location address in memory storage for each location in a scanning plane which is defined by the ultrasonic vibration transmission scanning, discriminator means for separating the echo signals from said ultrasonic probe which achieve a prerequisite amplitude from those echo signals which fail to achieve said prerequisite amplitude, comparator means connected to said discriminator means, to said address generator and to said memory storage locations for contemporaneously receiving from said discriminator means the echo signals which achieve said prerequisite amplitude as well as the location address corresponding to the location from which each such echo signal is received, and for transmitting to storage at the same memory storage location the greater of the aforesaid echo signal and the previously stored contents of said memory storage at the same address location, and circuit means connecting said discriminator means to memory storage, and responding to echo amplitude signals which fail to achieve said prerequisite amplitude for enhancing with such signals the existing stored contents of said memory storage locations at addresses corresponding to the respective locations from which such signal emanate, and then only at memory storage locations in which the previously stored contents fail to exceed said prerequisite amplitude.

3. The system of claim 2 wherein said means for enhancing the existing stored memory contents comprises an adder-normalizer circuit which accumulates the value of said echo amplitude signals failing to achieve said prerequisite amplitude, and normalizing said accumulated value by the number of occurrences of such echo amplitude signals thereby accumulated, and wherein the normalized value thereby obtained is stored in the appropriate memory storage location.

4. The system of claim 2 wherein analog to digital signal conversion means are employed to perform signal conversion of said echo signals prior to transmission to said discriminator means, and to perform signal conversion of inputs to said address generator from said probe position sensing means.

5. In an instrument for medical diagnosis having a transducer for transmitting vibrations at ultrasonic frequencies into the body of a patient and for detecting echoes produced by said vibrations at tissue interfaces within said patient and for generating responsive electrical echo signals, a position sensor for providing electrical indications of the position and orientation of said transducer, and a display unit for producing a two-dimensional visual representation of said tissue interfaces in a scanning plane, the improvement comprising a digital scan converter for receiving inputs from said position sensor and transducer and having a location determination means for assigning two-dimensional coordinates to locations in said scanning plane, means for accumulating the echo signals emanating from each two-dimensional coordinate location for which none of the echo signals achieves a predetermined amplitude, normalizing the signals thereby accumulated over the number of occurrences of such signals, and registering the normalized value thereby obtained, and means for registering only the largest echo signal emanating from those coordinate locations where at least one echo signal emanating therefrom achieves the aforesaid predetermined amplitude, with said scan converter transmitting to said display unit the signal values thereby registered to form said visual representation of said tissue interface.

6. An ultrasonic instrument for medical diagnostic imaging comprising an transducer for positioning in communication with a patient for transmitting penetrating ultrasonic vibrations to the patient's body and for detecting resultant echoes indicative of the location and nature of tissue interfaces in a scanning plane through the patient's body as defined by the position and orientation of said transducer when the associated echo is detected, and for producing characteristic echo signals, a digital scan converter including a multiplicity of addressable memory storage locations in communication with said display unit, transducer position sensing means, an address generator for receiving said echo signals and inputs from said transducer position sensing means to generate a digital location address in memory storage corresponding to the two-dimensional coordinates of a location in said scanning plane, means for producing digital representations of the amplitudes of echo signals received from said transducer, discriminator means for separating those echo signals received by said transducer which achieve a prerequisite amplitude from those echo signals which fail to achieve said prerequisite amplitude, a first comparator means connected to said discriminator means, to said address generator and to said memory storage for contemporaneously receiving an echo signal which achieves said prerequisite amplitude as well as the previously stored contents of the memory storage location corresponding to the coordinate location from which the associated echo emanates, and for transmitting to the same memory storage location the greater of the aforesaid echo signal and said previously stored contents, a second comparator means in communication with said address generator and memory storage for determining whether or not the previously stored contents of memory storage at the address location determined by said address generator achieves the aforesaid prerequisite amplitude and for generating an integration signal when the aforesaid previously stored contents fails to achieve said prerequisite amplitude, adder-normalizer means connected to said discriminator means, said memory storage, and said second comparator means and actuated by said integration signal to add echo signals to the previously stored contents of said memory storage at the associated memory storage address and average the sum thereby obtained over the number of occurrences of said added echo signals, and a display means connected to said memory storage for contemporaneously displaying visual representations of the contents of all of the memory storage locations.

7. In an instrument for medical diagnosis having a transducer for transmitting ultrasonic impulses into the body of the patient and for detecting echo information from tissue interfaces resulting from said impulses and generating in response thereto echo information signals, display means for producing a visual representation of said tissue interfaces in the plane of scanning movement of the transducer, the improvement which comprises a digital scan converter receiving the echo information signals and rendering the echo information signals compatible with the display means, said scan converter including both peak echo signal detection means and echo signal accumulation normalization means, with large echo signals having amplitudes above a prerequisite amplitude being processed by said peak detection means, and small echo signals below said prerequisite amplitude being processed by said accumulation-normalization means, whereby peak analysis is performed on larger signals while preserving image information carried upon small pulses and to improve the sensitivity of said instrument in distinguishing image information from noise.

8. An instrument as in claim 7, in which said scan converter further includes memory storage means having memory storage locations for storing echo signals at storage locations corresponding to coordinates in said scanning plane;
and in which said peak detection means cooperate with said memory means to compare with the previously stored contents at a location any new large echo signal for that location, and registering within said memory means the greater of the two;
and in which said accumulation-normalization means cooperates with said memory means to compare to the prerequisite amplitude the previously stored contents at the location of a new small echo signal, and if said stored contents are less than said prerequisite amplitude, registering in said memory means the value of the sum of the new small signal with the previously stored contents, normalized by the number of small signals which have been detected for said location.

9. An instrument as in claim 7, in which said transducer is scanned through an angle at a rate providing echo information in real time, with said angle defining said scanning plane and in which said digital scan converter includes means for calculating the location of said echo information by utilizing the angular orientation of said transducer.

10. A method of detecting the location of tissue interfaces in the body of a living subject using an ultrasonic imaging system employing a probe, probe position sensing means, and a display unit wherein image signals are registered at a multiplicity of spaced locations comprising: directing vibrations at ultrasonic frequencies from said probe into the body of the subject, detecting the occurrence and timing of the resulting echoes, associating specific two-dimensional coordinate positions in a plane transverse to the body of the subject with specific ones of said spaced locations in said display unit as determined by the positions of said probe ascertained from said probe position sensing means and as determined by the distances of the origin of the echoes from said probe as ascertained from said echo timing, registering as echo signals at each of the associated spaced locations on said display unit only the largest single echo at each one of the aforesaid multiplicity of spaced locations associated with a specific two-dimensional coordinate position at which any echo achieving a preselected prerequisite amplitude is detected, averaging the amplitudes of the echoes emanating from each two-dimensional coordinate position at which no echo achieves said prerequisite amplitude to obtain a normalized amplitude value, and registering said normalized amplitude value of echoes emanating from each two-dimensional coordinate position at which no echo achieves said prerequisite amplitude.

11. A method as in claim 10 which comprises the further step of adjusting said prerequisite amplitude to vary the distribution of echo signals above and below said prerequisite amplitude to obtain the optimum image on said display unit.

12. A method of detecting the location of tissue interfaces in the body of a living subject using an ultrasonic imaging system employing a probe, probe position sensing means, and a display unit wherein image signals are registered at a multiplicity of spaced locations comprising: directing vibrations at ultrasonic frequencies from said probe into the body of the subject, detecting the occurrence and timing of the resulting echoes, associating specific two-dimensional coordinate positions in a plane transverse to the body of the subject with specific ones of said spaced locations in said display unit as determined by the positions of said probe ascertained from said probe position sensing means and as determined by the distances of the origin of the echoes from said probe as ascertained from said echo timing, registering as echo signals at each of the associated spaced locations on said display unit only the largest single echo at each one of the aforesaid multiplicity of spaced locations associated with a specific two-dimensional coordinate position at which any echo achieving a preselected prerequisite amplitude is detected, accumulating the sum of the amplitudes of the echoes emanating from each two-dimensional coordinate position at which no echo achieves said prerequisite amplitude, averaging by the number of occurrences of such echoes at said position, and registering the normalized value of the amplitudes of echoes emanating from each two-dimensional coordinate position at which no echo achieves said prerequisite amplitude.

* * * * *